(12) United States Patent
Brun

(10) Patent No.: US 7,621,966 B2
(45) Date of Patent: *Nov. 24, 2009

(54) COSMETIC COMPOSITION COMPRISING AT LEAST ONE PIGMENT AND/OR AT LEAST ONE FILLER SURFACE-TREATED BEFOREHAND WITH AT LEAST ONE ORGANIC AGENT AND AT LEAST ONE ELECTROPHILIC MONOMER

(75) Inventor: Gaëlle Brun, Paris (FR)

(73) Assignee: L'Oreal S.A., Paris (FR)

( * ) Notice: Subject to any disclaimer, the term of this patent is extended or adjusted under 35 U.S.C. 154(b) by 126 days.

This patent is subject to a terminal disclaimer.

(21) Appl. No.: 11/544,576

(22) Filed: Oct. 10, 2006

(65) Prior Publication Data

US 2007/0089246 A1 Apr. 26, 2007

Related U.S. Application Data

(60) Provisional application No. 60/726,205, filed on Oct. 14, 2005.

(30) Foreign Application Priority Data

Oct. 7, 2005 (FR) .................................. 05 53061

(51) Int. Cl.
A61Q 5/10 (2006.01)
(52) U.S. Cl. ...................... 8/405; 8/552; 8/557; 8/558; 8/637.1
(58) Field of Classification Search ...................... 8/405, 8/552, 557, 558, 637.1
See application file for complete search history.

(56) References Cited

U.S. PATENT DOCUMENTS

| | | | |
|---|---|---|---|
| 2,748,050 A | 5/1956 | Shearer et al. | |
| 3,527,224 A | 9/1970 | Rabinowitz et al. | |
| 3,667,472 A | 6/1972 | Halpern | |
| 3,995,641 A | 12/1976 | Kronenthal et al. | |
| 4,035,334 A | 7/1977 | Davydov et al. | |
| 4,578,266 A | 3/1986 | Tietjen et al. | |
| 4,650,826 A | 3/1987 | Waniczek et al. | |
| 5,290,825 A | 3/1994 | Lazar | |
| 5,645,609 A | 7/1997 | Andrean et al. | |
| 5,990,479 A | 11/1999 | Weiss et al. | |
| 6,106,577 A * | 8/2000 | Audousset et al. | 8/403 |
| 6,224,622 B1 | 5/2001 | Kotzev | |
| 6,225,198 B1 | 5/2001 | Alivisatos et al. | |
| 2003/0175229 A1 * | 9/2003 | Giroud | 424/70.12 |
| 2004/0156800 A1 | 8/2004 | Brun et al. | |
| 2004/0253757 A1 | 12/2004 | Gourlaouen et al. | |

FOREIGN PATENT DOCUMENTS

| | | |
|---|---|---|
| EP | 1 184 426 B1 | 3/2002 |
| EP | 1 440 681 A1 | 7/2004 |
| FR | 2 679 771 A1 | 2/1993 |
| FR | 2 741 530 A1 | 5/1997 |
| FR | 2 833 489 A1 | 6/2003 |
| WO | WO 2004/043330 A2 | 5/2004 |

OTHER PUBLICATIONS

French Search Report for FR 0553061, dated Jul. 19, 2006.
B. O. Dabbousi et al., "(CdSe)ZnS Core-Shell Quantum Dots: Synthesis and Characterization of a Size Series of Highly Luminescent Nanocrystallites," J. Phys. Chem. B, vol. 101, pp. 9463-9475 (1997).
Xiaogang Peng et al., "Epitaxial growth of Highly Luminescent CdSe/CdS Core/Shell Nanocrystals with Photostability and Electronic Accessibility," J. Am. Chem. Soc., vol. 199, pp. 7019-7029 (1997).
Mitchell L. Schlossman, "Treated Pigments, New Ways to Impart Color on the Skin," Cosmetics & Toiletries, vol. 105, pp. 53-64 (1990).
Jerry March, "Carbocations, Carbanions, Free Radicals, Carbenes, and Nitrenes," Advanced Organic Chemistry, Reactions, Mechanisms, and Structure, Third Edition, John Wiley & Sons, pp. 141-178 (1985).
S.M. Sayyah et al, "Characterization and Gamma Radition Effects on Poly(methyl methacrylate) Doped with Some Benzylidine Polymers," Journal of Polymer Research, vol. 7, No. 2, pp. 97-106 (2000).
Von H. Hopff et al., "Über die Polymerisation des Methylenmalonsäthylesters," Makromoleculaire Chemie, pp. 95-105 (1961).
J.-L. de Keyser et al., "Poly(diethyl methylidenemalonate) Nanoparticles as a Potential Drug Carrier: Preparation, Distribution and Elimination after Intravenous and Peroral Administration to Mice," Journal of Pharmaceutical Sciences, vol. 80, No. 1, pp. 67-70 (1991).
Philip Klemarczyk, "A general synthesis of 1,1 disbustituted electron deficient olefins and their polymer properties," Polymer, vol. 39, No. 1, pp. 173-181 (1998).
P. Breton, "Physico-chemical characterization, preparation and performance of poly (methylidene malonate 2.1.2) nanoparticles," Biomaterials, vol. 19, pp. 271-281 (1998).
François Lescure, "Preparation and Characterization of Novel Poly(methylidene Malonate 2.1.2.)-Made Nanoparticles," Pharmaceutical Research, vol. 11, No. 9, pp. 1270-1277 (1994).
Aryeh Bachrach et al., "Anionic Oligomerization of Dimethyl Itaconate," European Polymer Journal, vol. 12, pp. 563-569 (1976).
E. Gipstein et al., "Synthesis and Polymerization of Alkyl α-(Alkylsulfonyl)acrylates," J. Org. Chem, vol. 45, pp. 1486-1489 (1980).

(Continued)

Primary Examiner—Eisa B Elhilo
(74) Attorney, Agent, or Firm—Finnegan, Henderson, Farabow, Garrett & Dunner, L.L.P.

(57) ABSTRACT

Disclosed herein is a composition for treating keratin materials, for example, keratin fibers, comprising, in a cosmetically acceptable medium, at least one electrophilic monomer and at least one pigment and/or at least one filler that have been surface-treated beforehand with at least one organic agent, wherein the at least one surface-treated pigment and/or the at least one surface-treated filler are not chosen from micas coated with titanium and with at least one organic pigment. Also disclosed herein is a process for treating keratin fibers comprising applying such a composition to the keratin fibers.

46 Claims, No Drawings

OTHER PUBLICATIONS

"Polymerization of Phenyl and Methyl Vinyl Sulfones with Anionic-Type Initiators," Journal of Polymer Science, Part A-1: Polymer Chemistry, vol. 9, Part A-1, No. 1, pp. 249-252 (1971).

Takashi Ishizone et al., "Controlled Anionic Polymerization of *tert*-Butyl Acrylate with Diphenylmethylpotassium in the Presence of Triethylborane," Macromolecules, vol. 32, pp. 955-957 (1999).

* cited by examiner

COSMETIC COMPOSITION COMPRISING AT LEAST ONE PIGMENT AND/OR AT LEAST ONE FILLER SURFACE-TREATED BEFOREHAND WITH AT LEAST ONE ORGANIC AGENT AND AT LEAST ONE ELECTROPHILIC MONOMER

This application claims benefit of U.S. Provisional Application No. 60/726,205, filed Oct. 14, 2005, the contents of which are incorporated herein by reference. This application also claims benefit of priority under 35 U.S.C. § 119 to French Patent Application No. FR 05 53061, filed Oct. 7, 2005, the contents of which are also incorporated herein by reference.

Disclosed herein is a composition for treating keratin materials such as the skin, the hair, the eyelashes, and/or the nails, for example, keratin fibers such as the hair, comprising, in a cosmetically acceptable medium, at least one electrophilic monomer and at least one pigment and/or at least one filler that have been surface-treated beforehand with at least one organic agent, wherein the at least one pigment or the at least one filler is not chosen from micas coated with titanium and with an organic pigment.

In the field of dyeing keratin fibers, it is known practice to dye keratin fibers via various techniques using direct dyes and/or pigments for non-permanent dyeing or dye precursors for permanent dyeing.

Non-permanent dyeing or direct dyeing comprises dyeing the keratin fibers with dye compositions comprising at least one direct dye. These dyes are colored and coloring molecules that have affinity for keratin fibers. They are applied to the keratin fibers for a time that is necessary to obtain the desired coloration, and are then rinsed off.

The standard dyes that are used may include, for example, nitrobenzene dyes, anthraquinone dyes, nitropyridine dyes, azo dyes, xanthene dyes, acridine dyes, azine dyes, triarylmethane dyes, and natural dyes.

Some of these dyes may be used under lightening conditions, which may make it possible to obtain visible colorations on dark hair.

It is also known practice to dye keratin fibers permanently by oxidation dyeing. This dyeing technique comprises applying to the keratin fibers a composition comprising at least one dye precursor such as oxidation bases and couplers. Under the action of an oxidizing agent, these precursors form at least one colored species in the hair.

The variety of molecules available as oxidation bases and couplers may allow a wide range of colors to be obtained, and the colorations resulting therefrom may be permanent, strong, and/or show good resistance to external agents such as light, bad weather, washing, perspiration, and/or rubbing.

In order to be visible on dark hair, these two dyeing techniques typically require prior or simultaneous bleaching of the keratin fibers. This bleaching step, which may be performed with an oxidizing agent such as hydrogen peroxide or persalts, may result in appreciable degradation of the keratin fibers, which may impair their cosmetic properties. The hair may then have a tendency to become coarse, more difficult to disentangle, and/or more brittle.

Another dyeing method comprises using pigments. Specifically, the use of pigment at the surface of keratin fibers generally makes it possible to obtain visible colorations on dark hair since the pigment at the surface masks the natural color of the fiber. The use of pigment to color keratin fibers is described, for example, in French Patent Application No. 2 741 530, which recommends the use for dyeing keratin fibers of a composition comprising at least one dispersion of film-forming polymer particles comprising at least one acid function and at least one pigment dispersed in the continuous phase of the dispersion.

The colorations obtained via this dyeing method may have the drawback of having poor shampoo fastness.

In the field of keratin fiber care, it is known practice to use fillers, which may give the keratin materials softness and sheen properties and, in the case of the hair, volume and smoothness. However, with standard treatment methods, the effects obtained are often insufficient in terms of efficacy and durability.

Hair treatment compositions using compositions comprising electrophilic monomers are described, for example, in French Patent Application No. 2 833 489. Such a composition may allow perfectly coated and non-greasy hair to be obtained.

It is also known from the prior art that the polymerization of electrophilic monomers may be accelerated with pigments or fillers. For example, U.S. Pat. No. 5,290,825 describes this phenomenon with alkyl cyanoacrylates.

It would therefore be desirable to provide compositions for treating keratin materials, for example, keratin fibers such as the hair, which may make it possible either to obtain visible colorations on a dark support without it being necessary to lighten or bleach the fibers, and which may show good shampoo fastness. It would also be desirable to provide compositions that may make it possible to obtain a care effect on keratin materials such as the hair that is sufficiently pronounced, long-lasting, and resistant to standard treatments such as shampooing.

Thus, disclosed herein is a composition for treating keratin materials, comprising, in a cosmetically acceptable medium, at least one electrophilic monomer and at least one pigment and/or at least one filler that have been surface-treated beforehand with at least one organic agent, wherein the at least one surface-treated pigment or the at least one surface-treated filler is not chosen from micas coated with titanium and with an organic pigment.

The composition in accordance with the present disclosure may make it possible, in the case of pigments, to improve the visibility of the colorations on a dark keratin material. For instance, in the case of dark keratin fibers, a very visible coloration may be obtained without it being necessary to lighten or bleach the keratin fibers and consequently without any physical degradation of the keratin fibers.

Furthermore, the coloration obtained may show good fastness with respect to the various attacking factors to which the hair may be subjected, such as shampooing, rubbing, light, bad weather, sweat, and/or permanent reshaping. These properties may be particularly noteworthy as concerns the shampoo fastness of the coloration. The coloration may be obtained in varied shades, and may be chromatic, strong, aesthetic, and/or sparingly selective. The hair moreover may show good cosmetic properties such as softness or a natural feel.

In the case of fillers, the compositions according to the present disclosure may make it possible to obtain a good level of softness on keratin materials, which is remanent over time and with respect to shampooing. Furthermore, good homogeneity of the effect on the keratin support may be observed.

Moreover, the surface treatment of the pigments and/or fillers present in the composition in accordance with the present disclosure may make it possible to obtain good stability of the composition in accordance with the present disclosure.

Also disclosed herein is a process for treating keratin fibers using the composition in accordance with the present disclosure, and also the use of this composition for treating keratin fibers.

Further disclosed herein is a treatment kit comprising, at least one pigment and/or at least one filler that have been surface-treated beforehand with at least one organic agent, and at least one electrophilic monomer.

In the context of the present disclosure, the at least one surface-treated pigment and/or the at least one surface-treated filler are not chosen from micas coated with titanium and with an organic pigment, i.e., the at least one surface-treated pigment and/or the at least one surface-treated filler are not chosen from micas coated with titanium surface-treated with an organic pigment.

Pigments

In at least one embodiment of the present disclosure, the pigments that have not been surface-treated have a solubility in water of less than 0.01%, for example, less than 0.0001% at 20° C., and an absorption ranging from 350 to 700 nm, and in at least one embodiment, an absorption with a maximum.

The pigment that has not been surface-treated, which is referred to hereinbelow as "pigment", may be an organic pigment. As used herein, the term "organic pigment" means any pigment that satisfies the definition in Ullmann's encyclopedia in the chapter on organic pigments. The organic pigment may be chosen, for example, from nitroso, nitro, azo, xanthene, quinoline, anthraquinone, phthalocyanin, metal complex, isoindolinone, isoindoline, quinacridone, perinone, perylene, diketopyrrolopyrrole, thioindigo, dioxazine, triphenylmethane, and quinophthalone compounds.

The at least one organic pigment may be chosen, for example, from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21100, 21108, 47000, and 47005, the green pigments codified in the Color Index under the references CI 61565, 61570, and 74260, the orange pigments codified in the Color Index under the references CI 11725, 15510, 45370, and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, and 75470, and the pigments obtained by oxidative polymerization of indole or phenolic derivatives as described, for example, in French Patent No. 2 679 771.

These pigments may also be in the form of composite pigments as described, for example, in European Patent No. 1 184 426. These composite pigments may be composed, for instance, of particles comprising an inorganic nucleus at least partially coated with an organic pigment and at least one binder to fix the organic pigments to the nucleus.

Other examples may include pigmentary pastes of organic pigments such as the products sold by the company Hoechst under the names:

Jaune Cosmenyl IOG: Pigment Yellow 3 (CI 11710);
Jaune Cosmenyl G: Pigment Yellow 1 (CI 11680);
Orange Cosmenyl GR: Pigment Orange 43 (CI 71105);
Rouge Cosmenyl R": Pigment Red 4 (CI 12085);
Carmine Cosmenyl FB: Pigment Red 5 (CI 12490);
Violet Cosmenyl RL: Pigment Violet 23 (CI 51319);
Bleu Cosmenyl A2R: Pigment Blue 15.1 (CI 74160);
Vert Cosmenyl GG: Pigment Green 7 (CI 74260); and
Noir Cosmenyl R: Pigment Black 7 (CI 77266).

The at least one pigment may also be chosen from lakes. As used herein, the term "lake" means insolubilized dyes adsorbed onto insoluble particles, the assembly thus obtained remaining insoluble during use.

The inorganic substrates onto which the dyes are adsorbed may include, for example, alumina, silica, calcium sodium borosilicate, calcium aluminum borosilicate, and aluminum.

Non-limiting examples of organic dyes include cochineal carmine and the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), and D&C Blue 1 (CI 42 090).

An additional non-limiting example of a lake is the product known under the following name: D&C Red 7 (CI 15 850:1).

The at least one pigment may also be a pigment with special effects. As used herein, the term "pigments with special effects" means pigments that generally create a non-uniform colored appearance (characterized by a certain shade, a certain vivacity, and/or a certain lightness) that changes as a function of the conditions of observation (light, temperature, observation angles, etc.). They thus contrast with white or colored pigments that afford a standard uniform opaque, semi-transparent, or transparent shade.

Two types of pigment with special effects exist: those with a low refractive index, such as fluorescent, photochromic, and thermochromic pigments, and those with a high refractive index, such as nacres and flakes.

Examples of pigments with special effects include, but are not limited to, nacreous pigments, for instance, white nacreous pigments such as mica coated with titanium or with bismuth oxychloride, colored nacreous pigments such as titanium mica with iron oxides, for example, titanium mica with ferric blue or with chromium oxide, titanium mica with an organic pigment of the abovementioned type, and also nacreous pigments based on bismuth oxychloride.

The at least one pigment may also be chosen from pigments with an interference effect that are not fixed onto a substrate, for instance, liquid crystals (Helicones HC from Wacker), and holographic interference flakes (Geometric Pigments or Spectra f/x from Spectratek). Pigments with special effects may also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known in the literature and may be manufactured according to the processes described, for example, in U.S. Pat. Nos. 6,225,198 and 5,990,479, in the publications cited therein, and also in the following publications: Dabboussi B.O. et al. "(CdSe)ZnS core-shell quantum dots: synthesis and characterization of a size series of highly luminescent nanocrystallites" *Journal of Physical Chemistry B*, vol. 101, 1997, pp. 9463-9475 and Peng, Xiaogang et al. "Epitaxial growth of highly luminescent CdSe/CdS core/shell nanocrystals with photostability and electronic accessibility", *Journal of the American Chemical Society*, vol. 119, No. 30, pp. 7019-7029.

The at least one pigment may also be a mineral pigment. As used herein, the term "mineral pigment" means any pigment that satisfies the definition in Ullmann's encyclopedia in the chapter on inorganic pigments. Non-limiting examples of mineral pigments that are useful in the present disclosure include zirconium oxides, cerium oxides, iron oxides, chromium oxides, manganese violet, ultramarine blue, chromium hydrate, ferric blue, and titanium dioxide. The following mineral pigments may also be used: $Ta_2O_5$, $Ti_3O_5$, $Ti_2O_3$, $TiO$, and $ZrO_2$ as a mixture with $TiO_2$, $ZrO_2$, $Nb_2O_5$, $CeO_2$, and ZnS.

The at least one pigment may also be a nacreous pigment such as white nacreous pigments, for example, mica coated with titanium or with bismuth oxychloride, colored nacreous pigments such as mica coated with titanium and with iron oxides, mica coated with titanium and, for example, with ferric blue or chromium oxide, mica coated with titanium and with an organic pigment as defined above, and also nacreous pigments based on bismuth oxychloride. Examples of such pigments may include the Cellini pigments sold by Engelhard (Mica-$TiO_2$-lake), Prestige sold by Eckart (Mica-$TiO_2$), and Colorona sold by Merck (Mica-$TiO_2$—Fe/$_2O_3$).

In addition to nacres on a mica support, multilayer pigments based on synthetic substrates such as alumina, silica, calcium sodium borosilicate, calcium aluminum borosilicates, and aluminum, may be useful in accordance with the present disclosure. The size of the at least one pigment may generally range from 10 nm to 200 μm, for example, from 20 nm to 80 μm, or from 30 nm to 50 μm.

Fillers

As used herein, the term "filler" means a substantially uncolored compound that is solid at room temperature and atmospheric pressure, and insoluble in the various ingredients of the composition, even when these ingredients are brought to a temperature above room temperature.

The at least one filler may be chosen from mineral and organic fillers. The at least one filler may be particles of any form, for example, platelet-shaped, spherical, and oblong, irrespective of their crystallographic form (for example lamellar, cubic, hexagonal, and orthorhombic).

Suitable fillers that may be used in the compositions according to the present disclosure may include, but are not limited to, talc; natural or synthetic mica; silica; kaolin; polyamides (Nylon®), poly-β-alanine and polyethylene powders; tetrafluoroethylene polymer (Teflon®) powders; lauroyllysine; starch; boron nitride; acrylic acid polymer powders; silicone resin microbeads, for instance "Tospearls®" from the company Toshiba; bismuth oxychlorides; precipitated calcium carbonate; magnesium carbonate and magnesium hydrogen carbonate; hydroxyapatite; hollow silica microspheres such as "Silica Beads SB 700®" and "Silica Beads SB 700®" from the company Maprecos, "Sunspheres H-33®" and "Sunspheres H-51®" from the company Asahi Glass; acrylic polymer microspheres such as those made from crosslinked acrylate copolymer "Polytrap 6603 Adsorber®" from the company RP Scherrer and those made from polymethyl methacrylate "Micropearl M100®" from the company SEPPIC; polyurethane powders such as the hexamethylene diisocyanate and trimethylol hexyl lactone copolymer powder sold under the name "Plastic Powder D-400®" by the company Toshiki; glass or ceramic microcapsules; metal soaps derived from organic carboxylic acids containing from 8 to 22 carbon atoms, for instance, from 12 to 18 carbon atoms, for example zinc stearate, magnesium stearate, lithium stearate, zinc laurate, and magnesium myristate; microcapsules of methyl acrylate or methacrylate polymers or copolymers, or alternatively, vinylidene chloride and acrylonitrile copolymers, for instance "Expancel®" from the company Expancel; elastomeric crosslinked organopolysiloxane powders such as those sold under the name "Trefil Powder E-506C" by the company Dow Corning; and mixtures thereof.

The at least one filler, surface-treated or otherwise, may have an apparent diameter ranging from 0.01 to 150 μm, for example, from 0.5 to 150 μm. As used herein, the term "apparent diameter" corresponds to the diameter of the circle in which is inscribed the elementary particle along its smallest dimension (thickness for lamellae).

The pigments and fillers that have been surface-treated beforehand, which are useful in the context of the present disclosure may be chosen from pigments and fillers that have totally or partially undergone a surface treatment chosen from chemical, electronic, electrochemical, mechanochemical, and mechanical surface treatments, with at least one organic agent such as those described, for example, in Cosmetics and Toiletries, February 1990, vol. 105, pp. 53-64, before being dispersed in the composition in accordance with the present disclosure. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol, and lauric acid and derivatives thereof; anionic surfactants; lecithins; sodium, potassium, magnesium, iron, titanium, zinc, and aluminum salts of fatty acids, for example aluminum stearate and laurate; metal alkoxides; polysaccharides, for example chitosan, cellulose, and derivatives thereof; polyethylene; (meth)acrylic polymers, for example polymethyl methacrylates; polymers and copolymers comprising acrylate units; proteins; alkanolamines; silicone compounds comprising acrylate units; proteins; alkanolamines; silicone compounds, for example silicones, polydimethylsiloxanes, alkoxysilanes, alkylsilanes, and siloxysilicates; organofluorine compounds, for example perfluoroalkyl ethers; and fluorosilicone compounds.

For the purposes of the present disclosure, the surface treatment is such that a surface-treated pigment conserves its intrinsic pretreatment pigmenting properties and a surface-treated filler conserves its intrinsic pretreatment filling properties. For example, the inorganic substrates such as alumina and silica onto which are adsorbed organic dyes are not surface-treated fillers for the purposes of the present disclosure.

In at least one embodiment, the surface-treated pigments and fillers that are useful in the context of the present disclosure may also have been treated with a mixture of these compounds and/or may have undergone several surface treatments.

The surface-treated pigments and fillers that are useful in the context of the present disclosure may be prepared according to surface-treatment techniques that are known to those skilled in the art, or may be commercially available in the required form.

According to one embodiment of the present disclosure, the surface-treated pigments and/or fillers are coated with at least one organic layer.

The at least one organic agent with which the pigments and fillers are treated may be deposited on the pigments or fillers by any known method, for example, evaporation of solvent, chemical reaction between the molecules of the surface agent or creation of a covalent bond between the surface agent and the pigments or fillers.

The surface treatment may thus be performed, for example, by chemical reaction of at least one surface agent with the surface of the pigments or fillers and creation of a covalent bond between the at least one surface agent and the pigments or fillers. This method is described, for example, in U.S. Pat. No. 4,578,266.

In at least one embodiment, at least one organic agent covalently bonded to the pigments or fillers may be used.

The at least one agent for the surface treatment may be present in the composition in an amount ranging from 0.1% to 50% by weight, for example, from 0.5% to 30% by weight, or from 1% to 10% by weight relative to the total weight of the surface-treated pigments or fillers.

According to one embodiment of the present disclosure, the at least one surface treatment of the pigments and fillers may be chosen from the following treatments:

PEG-silicone treatments, for instance the AQ surface treatment sold by LCW;
chitosan treatments, for instance the CTS surface treatment sold by LCW;
triethoxycaprylylsilane treatments, for instance the AS surface treatment sold by LCW;
methicone treatments, for instance the SI surface treatment sold by LCW;
dimethicone treatments, for instance the Covasil 3.05 surface treatment sold by LCW;
dimethicone/trimethyl siloxysilicate treatments, for instance the Covasil 4.05 surface treatment sold by LCW;
lauroyllysine treatments, for instance the LL surface treatment sold by LCW;
lauroyllysine dimethicone treatments, for instance the LL/SI surface treatment sold by LCW;
magnesium myristate treatments, for instance the MM surface treatment sold by LCW;
aluminium dimyristate treatments, for instance the Ml surface treatment sold by Miyoshi;
perfluoropolymethyl isopropyl ether treatments, for instance the FHC surface treatment sold by LCW;
isostearyl sebacate treatments, for instance the HS surface treatment sold by Miyoshi;
disodium stearoyl glutamate treatments, for instance the NAI surface treatment sold by Miyoshi;
dimethicone/disodium stearoyl glutamate treatments, for instance the SA/NAI surface treatment sold by Miyoshi;
perfluoroalkyl phosphate treatments, for instance the PF surface treatment sold by Daito;
acrylate/dimethicone copolymer and perfluoroalkyl phosphate treatments, for instance the FSA treatment sold by Daito;
polymethylhydrogenosiloxane/perfluoroalkyl phosphate treatments, for instance the FS01 surface treatment sold by Daito;
lauroyllysine/aluminium tristearate treatments, for instance the LL-AISt surface treatment sold by Daito;
octyltriethylsilane treatments, for instance the OTS surface treatment sold by Daito;
octyltriethylsilane/perfluoroalkyl phosphate treatments, for instance the FOTS surface treatment sold by Daito;
acrylate/dimethicone copolymer treatments, for instance the ASC surface treatment sold by Daito;
isopropyl titanium triisostearate treatments, for instance the ITT surface treatment sold by Daito;
microcrystalline cellulose and carboxymethylcellulose treatments, for instance the AC surface treatment sold by Daito;
cellulose treatments, for instance the C2 surface treatment sold by Daito;
acrylate copolymer treatments, for instance the APD surface treatment sold by Daito; and
perfluoroalkyl phosphate/isopropyl titanium triisostearate treatments, for instance the PF+ITT surface treatment sold by Daito.

The at least one surface-treated pigment may be present in the composition in total amounts generally ranging from 0.05% to 50% by weight, for example, from 0.1% to 35% by weight, or from 0.5% to 20% by weight relative to the total weight of the composition.

The at least one surface-treated or surface-untreated filler may be present in the composition in total amounts ranging from 0.05% to 95% by weight, for example, from 0.1% to 50% by weight, or from 0.5% to 30% by weight relative to the total weight of the composition.

According to at least one embodiment, the composition in accordance with the present disclosure may further comprise at least one surface-untreated filler.

In another embodiment, the composition in accordance with the present disclosure may further comprise at least one surface-untreated pigment.

Electrophilic Monomers

As used herein, the term "electrophilic monomer" means a monomer capable of polymerizing via anionic polymerization in the presence of at least one nucleophilic agent.

As used herein, the term "anionic polymerization" means the mechanism defined in the book "Advanced Organic Chemistry", 3rd edition, by Jerry March, pages 151 to 161.

The at least one nucleophilic agent capable of initiating the anionic polymerization may be chosen from known systems capable of generating a carbanion on contact with an electrophilic agent, such as the hydroxide ions contained in water at neutral pH. As used herein, the term "carbanion" means the chemical species defined in the book "Advanced Organic Chemistry", 3rd edition, by Jerry March, page 141.

The at least one electrophilic monomer present in the composition of the present disclosure may be chosen, for example, from:

the benzylidene malononitrile derivatives (A), 2-(4-chlorobenzylidene)malononitrile (A1), ethyl 2-cyano-3-phenylacrylate (B), and ethyl 2-cyano-3-(4-chlorophenyl)acrylate (B1) described, for instance, in Sayyah, *J Polymer Research*, 2000, p. 97:

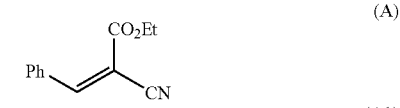

(A)

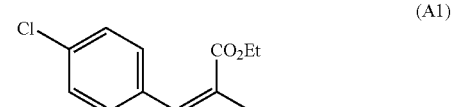

(A1)

(B)

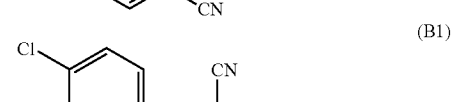

(B1)

methylidenemalonate derivatives, for instance diethyl 2-methylenemalonate (C) described by Hopff, *Makromoleculare Chemie*, 1961, p. 95, De Keyser, *J. Pharm. Sci*, 1991, p. 67 and Klemarczyk, *Polymer*, 1998, p. 173:

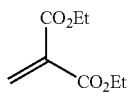

(C)

ethyl 2-ethoxycarbonylmethylenecarbonylacrylate (D) described, for example, by Breton, *Biomaterials*, 1998, p. 271 and Couvreur, *Pharmaceutical Research*, 1994, p. 1270:

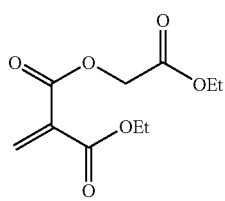

(D)

itaconate and itaconimide derivatives, for instance dimethyl itaconate (E) described by Bachrach, *European Polymer Journal*, 1976, p. 563, and N-butyl itaconimide (F), N-(4-tolyl)itaconimide (G), N-(2-ethylphenyl)itaconimide (H), N-(2,6-diethylphenyl)itaconimide (I) described, for instance, by Wanatabe, *J. Polymer Science*: Part: *Polymer chemistry*, 1994, p. 2073:

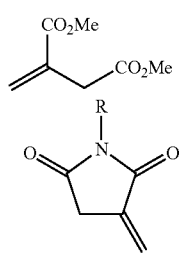

(E)

R=Butyl (F), 4-tolyl (G), 2-ethylphenyl (H), 2,6-diethylphenyl (I)

the derivatives methyl α-(methylsulfonyl)acrylate (K), ethyl α-(methylsulfonyl)acrylate (L), methyl α-(tert-butylsulfonyl)acrylate (M), tert-butyl α-(methylsulfonyl) acrylate (N) and tert-butyl α-(tert-butylsulfonyl)acrylate (O), described, for example, by Gipstein, *J. Org. Chem*, 1980, p. 1486, and the derivatives 1,1-bis(methylsulfonyl)ethylene (P), 1-acetyl-1-methylsulfonylethylene (Q), methyl α-(methylsulfonyl)vinylsulfonate (R), and α-methylsulfonylacrylonitrile (S) described, for instance, in U.S. Pat. No. 2,748,050:

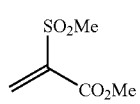

(K)

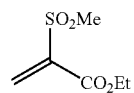

(L)

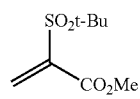

(M)

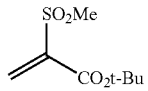

(N)

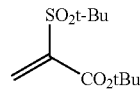

(O)

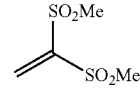

(P)

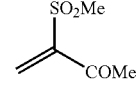

(Q)

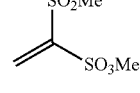

(R)

(S)

the methyl vinyl sulfone (T) and phenyl vinyl sulfone (U) derivatives described, for example, by Boor, *J Polymer Science*, 1971, p. 249:

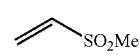

(T)

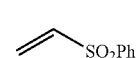

(U)

the phenyl vinyl sulfoxide derivative (V) described, for instance, by Kanga, *Polymer* preprints (ACS, Division of Polymer Chemistry), 1987, p. 322:

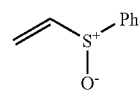

(V)

the derivative 3-methyl-N-(phenylsulfonyl)-1-aza-1,3-butadiene (W) described, for example, by Bonner, *Polymer Bulletin*, 1992, p. 517:

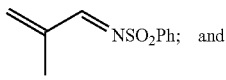

acrylate and acrylamide derivatives, for instance:

N-propyl-N-(3-triisopropoxysilylpropyl)acrylamide (X) and N-propyl-N-(3-triethoxysilylpropyl)acrylamide (Y) described, for instance, by Kobayashi, *Journal of Polymer Science*, Part: *Polymer Chemistry*, 2005, p. 2754:

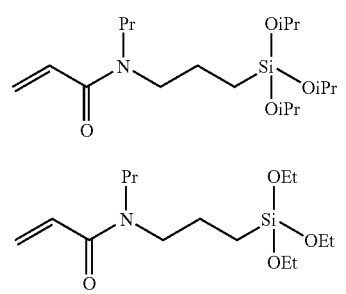

2-hydroxyethyl acrylate (Z) and 2-hydroxyethyl methacrylate (AA) described, for example, by Rozenberg, *International Journal of Plastics Technology*, 2003, p. 17:

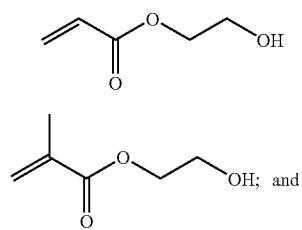

N-butyl acrylate (AB) by Schmitt, *Macromolecules*, 2001, p. 2115 and tert-butyl acrylate (AC) described, for instance, by Ishizone, *Macromolecules*, 1999, p. 955:

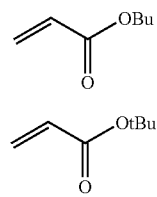

The at least one electrophilic monomer that is useful in accordance with the present disclosure may be chosen from cyclic and linear electrophilic monomers. When it is cyclic, in at least one embodiment, the electron-withdrawing group is exocyclic, i.e., it does not form an integral part of the cyclic structure of the monomer.

According to one embodiment of the present disclosure, the at least one electrophilic monomer that is useful in accordance with the present disclosure comprises at least two electron-withdrawing groups.

According to another embodiment of the present disclosure, the electrophilic monomers are chosen from the compounds of formula (I):

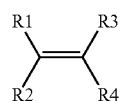

wherein:

$R_1$ and $R_2$, which may be identical or different, are chosen from sparingly electron-withdrawing or non-electron-withdrawing groups (sparingly inductive-withdrawing or non-inductive-withdrawing), including, but not limited to:

hydrogen atoms, saturated or unsaturated, linear, branched, or cyclic hydrocarbon-based groups comprising, for example, from 1 to 20, or from 1 to 10 carbon atoms, and optionally comprising at least one atom chosen from nitrogen, oxygen, and sulfur atoms, and optionally substituted with at least one group chosen from —OR, —COOR, —COR, —SH, —SR, and —OH, and halogen atoms, modified or unmodified polyorganosiloxane residues, and polyoxyalkylene groups;

$R_3$ and $R_4$, which may be identical or different, are chosen from electron-withdrawing (or inductive-withdrawing) groups including, but not limited to, —N($R_3^+$), —S($R)_2^+$, —$SH_2^+$, —$NH_3^+$, —$NO_2$, —$SO_2R$, —C≡N, —COOH, —COOR, —COSR, —$CONH_2$, —CONHR, —F, —Cl, —Br, —I, —OR, —COR, —SH, —SR, and —OH groups, linear or branched alkenyl groups, linear or branched alkynyl groups, $C_1$-$C_4$ monofluoroalkyl or polyfluoroalkyl groups, aryl groups such as phenyl, and aryloxy groups such as phenoxyloxy;

R is chosen from saturated or unsaturated, linear, branched, or cyclic hydrocarbon-based groups comprising, for example, from 1 to 20, or from 1 to 10 carbon atoms, and optionally comprising at least one atom chosen from nitrogen, oxygen, and sulfur atoms, and optionally substituted with at least one group chosen from —OR', —COOR', —COR', —SH, —SR', and —OH, halogen atoms, and polymer residues, this polymer possibly being obtained by a method chosen from free-radical polymerization, polycondensation, and ring opening, wherein R' is chosen from $C_1$-$C_{10}$ alkyl radicals.

As used herein, the term "electron-withdrawing or inductive-withdrawing group (—I)" means any group that is more electronegative than carbon. Reference may be made, for example, to the publication P. R. Wells, Prog. Phys. Org. Chem., vol. 6 111 (1968).

As used herein, the term "sparingly electron-withdrawing or non-electron-withdrawing group" means any group whose electronegativity is less than or equal to that of carbon.

In at least one embodiment, the alkenyl and/or alkynyl groups may comprise from 2 to 20 carbon atoms, for example, from 2 to 10 carbon atoms.

Non-limiting examples of saturated or unsaturated, linear, branched, or cyclic hydrocarbon-based groups comprising, for example, from 1 to 20 carbon atoms, or from 1 to 10 carbon atoms include linear or branched alkyl, alkenyl, and alkynyl groups, such as methyl, ethyl, n-butyl, tert-butyl, isobutyl, pentyl, hexyl, octyl, butenyl, and butynyl groups; cycloalkyl groups; and aromatic groups.

Examples of substituted hydrocarbon-based groups include, but are not limited to, hydroxyalkyl and polyhaloalkyl groups.

Examples of unmodified polyorganosiloxanes include, but are not limited to, polyalkylsiloxanes such as polydimethylsiloxanes, polyarylsiloxanes such as polyphenylsiloxanes, and polyarylalkylsiloxanes such as polymethylphenylsiloxanes.

Suitable modified polyorganosiloxanes include, for example, polydimethylsiloxanes comprising at least one group chosen from polyoxyalkylene, siloxy, silanol, amine, imine, and/or fluoroalkyl groups.

Non-limiting examples of polyoxyalkylene groups include polyoxyethylene groups and polyoxypropylene groups comprising, for example, from 1 to 200 oxyalkylene units.

Examples of monofluoroalkyl or polyfluoroalkyl groups include, but are not limited to, $-(CH_2)_n-(CF_2)_m-CF_3$ and $-(CH_2)_n-(CF_2)_m-CHF_2$ groups, wherein n=1 to 20 and m=1 to 20.

The substituents $R_1$ to $R_4$ may optionally be substituted with a group having cosmetic activity. The cosmetic activities may be obtained, for example, from groups having coloring, antioxidant, UV-screening, and/or conditioning functions.

Groups having a coloring function may be chosen, for example, from azo, quinone, methine, cyanomethine, and triarylmethane groups.

Non-limiting examples of groups having an antioxidant function include butylhydroxyanisole (BHA), butylhydroxytoluene (BHT), and vitamin E groups.

Examples of groups having a UV-screening function include, but are not limited to, benzophenone, cinnamate, benzoate, benzylidenecamphor, and dibenzoylmethane groups.

Suitable groups having a conditioning function may be chosen, for example, from cationic groups and groups of fatty ester type.

According to one embodiment of the present disclosure, the at least one electrophilic monomer is chosen from monomers of the cyanoacrylate family of formula (II):

wherein:
X is chosen from NH, S, and O;
$R'_3$ is chosen from hydrogen and R groups;
R, $R_1$, and $R_2$ are as defined above.

In at least one embodiment, in formulas (I) and (II), $R_1$ and $R_2$ are hydrogen.

According to another embodiment, in formula (II), X is O and $R'_3$ is chosen from $C_6$-$C_{10}$ alkyl radicals.

Compounds of formula (II) may be chosen, for example, from the monomers:

a) belonging to the family of polyfluoroalkyl 2-cyanoacrylates, such as the ester 2,2,3,3-tetrafluoropropyl 2-cyano-2-propenoate of formula (III):

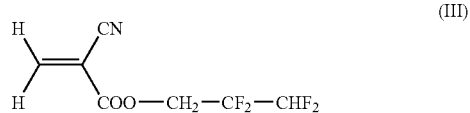

and the ester 2,2,2-trifluoroethyl 2-cyano-2-propenoate of formula (IV):

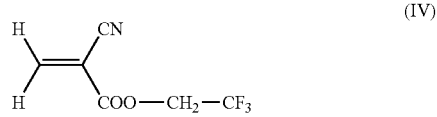

b) belonging to the alkyl or alkoxyalkyl 2-cyanoacrylate family of formula (VI):

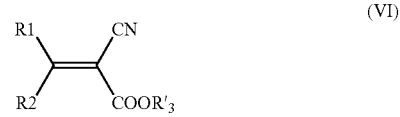

wherein:
$R'_3$ is chosen from $C_1$-$C_{10}$ alkyl radicals, $C_2$-$C_{10}$ alkenyl radicals, and $(C_1$-$C_4)$alkoxy$(C_1$-$C_{10})$ alkyl radicals, for instance, $C_1$-$C_{10}$ alkyl radicals and $(C_1$-$C_4)$alkoxy$(C_1$-$C_{10})$alkyl radicals; and
$R_1$ and $R_2$ are as defined above.

According to one embodiment, the compounds of formula (II) may be chosen, for example, from ethyl 2-cyanoacrylate, methyl 2-cyanoacrylate, n-propyl 2-cyanoacrylate, isopropyl 2-cyanoacrylate, tert-butyl 2-cyanoacrylate, n-butyl 2-cyanoacrylate, isobutyl 2-cyanoacrylate, 3-methoxybutyl cyanoacrylate, n-decyl cyanoacrylate, hexyl 2-cyanoacrylate, 2-ethoxyethyl 2-cyanoacrylate, 2-methoxyethyl 2-cyanoacrylate, 2-octyl 2-cyanoacrylate, 2-propoxyethyl 2-cyanoacrylate, n-octyl 2-cyanoacrylate, allyl 2-cyanoacrylate, methoxypropyl 2-cyanoacrylate, and isoamyl cyanoacrylate.

In another embodiment, in formula (VI), $R'_3$ may be chosen from $C_6$-$C_{10}$ alkyl radicals and $R_1$ and $R_2$ are hydrogen.

In yet another embodiment, the at least one electrophilic monomer is chosen from the monomers defined in b).

In a further embodiment, the at least one electrophilic monomer may be chosen from compounds of formula (VII) and mixtures thereof:

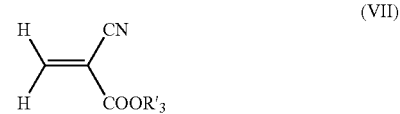

wherein $R'_3$ is chosen from the following radicals:
$-(CH_2)_7-CH_3$;
$-CH(CH_3)-(CH_2)_5-CH_3$;

—CH2—CH(C$_2$H$_5$)—(CH$_2$)$_3$—CH$_3$;
—(CH$_2$)$_5$—CH(CH$_3$)—CH$_3$; and
—(CH$_2$)$_4$—CH(C$_2$H$_5$)—CH$_3$.

The monomers used in accordance with the present disclosure may be covalently bonded to supports such as polymers, oligomers, and dendrimers. The polymer or the oligomer may be linear, branched, in comb form, or in block form. The distribution of the monomers of the present disclosure over the polymeric, oligomeric, or dendritic structure may be random, in an end position, or in the form of blocks.

The at least one electrophilic monomer is generally present in the composition in accordance with the present disclosure in an amount ranging from 0.1% to 80% by weight, for example, from 1% to 50% by weight relative to the total weight of the composition.

The at least one electrophilic monomer that is useful in the context of the present disclosure may be synthesized according to the known methods described in the literature. For example, the monomer of the cyanoacrylate family may be synthesized according to the teaching of U.S. Pat. Nos. 3,527,224, 3,591,767, 3,667,472, 3,995,641, 4,035,334, and 4,650,826.

According to one embodiment of the present disclosure, the at least one electrophilic monomer may be chosen from monomers capable of polymerizing on keratin fibers under cosmetically acceptable conditions. For example, the polymerization of the at least one monomer may take place at a temperature of less than or equal to 80° C., for instance, ranging from 10 to 80° C., or from 20 to 80° C., which does not prevent the application from being completed by drying under a hood, blow-drying, and/or treatment with a flat iron and/or a crimping iron.

The at least one nucleophilic agent may be applied independently of the composition of the present disclosure. The at least one nucleophilic agent may also be added to the composition of the present disclosure at the time of use. In this case, the composition in accordance with the present disclosure also comprises at least one nucleophilic agent.

According to another embodiment of the present disclosure, the at least one nucleophilic agent is chosen from molecular compounds, oligomers, dendrimers, and polymers bearing at least one nucleophilic function chosen from R$_2$N$^-$, NH$_2$$^-$, Ph$_3$C$^-$, R$_3$C$^-$, PhNH$^-$, pyridine, ArS$^-$, R—C≡C$^-$, RS$^-$, SH$^-$, RO$^-$, R$_2$NH, ArO$^-$, N$_3$$^-$, OH$^-$, ArNH$_2$, NH$_3$, I$^-$, Br$^-$, Cl$^-$, RCOO$^-$, SCN$^-$, ROH, RSH, NCO$^-$, CN$^-$, NO$_3$$^-$, ClO$_4$$^-$, and H$_2$O, wherein Ph is a phenyl group, Ar is an aryl group and R is chosen from C$_1$-C$_{10}$ alkyl groups.

In at least one embodiment, the at least one nucleophilic group is water.

Cosmetically Acceptable Medium

The cosmetically acceptable medium of the composition of the present disclosure may be in the form of an anhydrous and non-hygroscopic medium. As used herein, the term "anhydrous medium" means a medium containing less than 1% water.

According to one embodiment, the cosmetically acceptable medium of the composition of the present disclosure may be chosen from:
aromatic alcohols such as benzyl alcohol;
fatty alcohols;
modified or unmodified polyols such as glycerol, glycol, propylene glycol, dipropylene glycol, butylene glycol, and butyl diglycol;
volatile or non-volatile silicones, such as cyclopentasiloxane, cyclohexasiloxane, polydimethylsiloxanes possibly modified with at least one function chosen from phenyl, siloxy, silanol, amine, imine, fluoroalkyl, carboxylic, betaine, and/or quaternary ammonium functions;
mineral, organic, and plant oils;
oxyethylenated or non-oxyethylenated waxes, paraffins, and alkanes, for example, C$_5$-C$_{10}$ alkanes;
fatty acids, fatty amides, and fatty esters, for example, fatty alkyl benzoates and salicylates;
and mixtures thereof.

The cosmetically acceptable medium of the composition of the present disclosure may also be in the form of a direct and/or inverse emulsion and/or may be encapsulated, the electrophilic monomers being maintained in an anhydrous medium until the time of use. The dispersed or continuous phase of the emulsion may comprise water, at least one C$_1$-C$_4$ aliphatic alcohol and/or silicone, and mixtures thereof. The capsules or microcapsules containing the composition of the present disclosure may be dispersed in a medium chosen from anhydrous media as defined above, water, C$_1$-C$_4$ aliphatic alcohols, and mixtures thereof.

The composition in accordance with the present disclosure may also comprise at least one polymerization inhibitor.

The at least one polymerization inhibitor may be chosen from anionic and/or radical polymerization inhibitors.

Examples of anionic and/or radical polymerization inhibitors include, but are not limited to, sulfur dioxide, nitric oxide, organic acids such as a sulfonic acid, phosphoric acid, and acetic acid, lactone, boron trifluoride, hydroquinone and derivatives thereof such as hydroquinone monoethyl ether and tert-butylhydroquinone, benzoquinone and derivatives thereof such as duroquinone, catechol and derivatives thereof such as t-butylcatechol and methoxycatechol, anisole and derivatives thereof, such as methoxyanisole and hydroxyanisole, pyrogallol and derivatives thereof, p-methoxyphenol, butylhydroxytoluene, alkyl sulfates, alkyl sulfites, alkyl sulfones, alkyl sulfoxides, alkyl sulfides, mercaptans, 3-sulfonene, and mixtures thereof. In at least one embodiment, the alkyl groups may be chosen from groups comprising from 1 to 6 carbon atoms.

The at least one polymerization inhibitor is generally present in the composition in accordance with the present disclosure in an amount ranging from 0.01% to 10% by weight relative to the total weight of the composition, for example, from 0.05% to 5% by weight relative to the total weight of the composition.

The composition in accordance with the present disclosure may also comprise at least one thickening polymer that has no reactivity on the at least one electrophilic monomer that is useful in the context of the present disclosure.

Non-limiting examples of thickening polymers with no reactivity on the at least one electrophilic monomer used in the context of the present disclosure include polymethyl methacrylate-based (PMMA) and cyanoacrylate-based copolymers as described, for example in U.S. Pat. No. 6,224,622.

The at least one thickening polymer is generally present in the composition in accordance with the present disclosure in an amount ranging from 0.1% to 50%, for example, from 0.5% to 25%. They are useful, inter alia, for modulating the rate of polymerization of the electrophilic monomers.

The composition in accordance with present disclosure may also comprise additional compounds conventionally used in cosmetics. These compounds may be chosen, for example, from reducing agents, fatty substances, organomodified or non- organomodified silicones, thickeners other than the thickening polymers defined above, cationic, anionic, neutral, or amphoteric polymers, softeners, antifoams, moisturizers, emollients, basifying agents, antioxidants, free-radical scavengers, chelating agents, antidandruff agents, seborrhoea-regulating agents, calmatives, plasticizers, sunscreens, direct dyes (natural or unnatural), oxidation dyes (bases and/or couplers), pigments, mineral fillers, clays, colloidal minerals, nacres, fragrances, peptizers, preserving agents, anionic, cationic, amphoteric, zwitterionic, or nonionic surfactants, fixing or non-fixing polymers, conditioning polymers, hydrolyzed or non-hydrolyzed proteins, enzymes, amino acids, oligopeptides, peptides, vitamins, saccharides, oligosaccharides, polysaccharides, which may be hydrolysed or non-hydrolysed, and modified or unmodified, polyamino acids, branched or unbranched fatty alcohols, animal, plant or mineral waxes, ceramides, pseudoceramides, hydroxylated organic acids, polyisobutenes and poly(α-olefins), fatty esters, anionic polymers in dissolved or dispersed form, and nonionic polymers in dissolved or dispersed form.

It is to be understood that a person skilled in the art will take care to select the at least one optional additional compound such that the advantageous properties intrinsically associated with the composition in accordance with the present disclosure are not, or are not substantially, adversely affected by the envisaged addition.

The composition in accordance with the present disclosure may be in various forms, such as lotions, sprays, and mousses, and may be applied in the form of a shampoo and/or a hair conditioner.

The composition in accordance with the present disclosure may also comprise a propellant. The propellant generally comprises a compressed or liquefied gas usually used for the preparation of aerosol compositions. In at least one embodiment, the compressed or liquefied gas is chosen from air, carbon dioxide, compressed nitrogen, soluble gases such as dimethyl ether, halogenated hydrocarbons such as fluorohydrocarbons, non-halogenated hydrocarbons, and mixtures thereof.

The composition in accordance with the present disclosure may be in its native form or may result from the mixing of two compositions at the time of use. For example, the first composition may comprise the at least one electrophilic monomer and the second composition may comprise the at least one surface-treated pigment and/or at least one surface-treated filler.

The process according to the present disclosure comprises applying to keratin fibers a composition comprising, in a cosmetically acceptable medium, at least one pigment and/or one filler that have been surface-treated beforehand and at least one electrophilic monomer as defined above in the presence of at least one nucleophilic agent.

According to one embodiment, the application of the composition in accordance with the present disclosure is performed in at least two steps, wherein one of the steps comprises applying to the keratin fibers a composition comprising the at least one surface-treated pigment and/or at least one surface-treated filler, and the other step comprises applying to the keratin fibers a composition comprising at least one electrophilic monomer, the order of the steps being irrelevant.

The at least one nucleophilic agent that is useful may be used pure, as a solution, or in the form of an emulsion, or may be encapsulated. It may be present in the composition comprising the at least one surface-treated pigment. It may also be applied separately. In this case, it is possible, for example, to preimpregnate the keratin fibers using the at least one nucleophilic agent.

When the at least one nucleophilic agent is water, it is possible to premoisten the keratin fibers with an aqueous solution whose pH has been adjusted using acidifying and/or basifying agents.

Examples of acidifying agents include, but are not limited to, mineral or organic acids, for instance hydrochloric acid, orthophosphoric acid, sulfuric acid, carboxylic acids, for instance acetic acid, tartaric acid, citric acid, and lactic acid, and sulfonic acids.

Non-limiting examples of basifying agents include aqueous ammonia, alkaline carbonates, alkanolamines such as monoethanolamine, diethanolamine, and triethanolamine and derivatives thereof, sodium hydroxide, potassium hydroxide and the compounds of formula (VII) below:

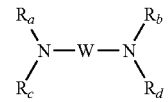

(VII)

wherein W is a propylene residue optionally substituted with at least one entity chosen from hydroxyl groups and $C_1$-$C_4$ alkyl radicals; and $R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

According to one embodiment of the present disclosure, the nucleophilicity of the keratin fibers may be increased by chemical transformation of the keratin fiber. For example, at least one keratin-reducing agent may be applied to the keratin fibers, before the application of the composition in accordance with the present disclosure, in order to reduce the disulfide bridges, of which keratin is partly composed, to thiols.

Examples of keratin-reducing agents that are useful include, but are not limited to:
  anhydrous sodium thiosulfate,
  powdered sodium metabisulfite,
  thiourea,
  ammonium sulfite,
  thioglycolic acid,
  thiolactic acid,
  ammonium thiolactate,
  glyceryl monothioglycolate,
  ammonium thioglycolate,
  thioglycerol,
  2,5-dihydroxybenzoic acid,
  diammonium dithioglycolate,
  strontium thioglycolate,
  calcium thioglycolate,
  zinc formosulfoxylate,
  isooctyl thioglycolate,
  dl-cysteine, and
  monoethanolamine thioglycolate.

In order to improve, inter alia, the adhesion of the polycyanoacrylate formed in situ, the keratin fibers may be pretreated with polymers of any type, or a hair treatment may be performed, for instance a direct dyeing, oxidation dyeing, permanent-waving, and/or hair relaxing operation.

The application of the compositions to the keratin fibers may or may not be followed by rinsing and/or drying. The drying may be performed with a drying hood, a hairdryer, and/or a smoothing iron.

These compositions may also contain various additional compounds as defined above.

According to the process in accordance with the present disclosure, it is possible to perform multiple superpositions of applications.

Also disclosed herein is a kit for treating keratin fibers, which contains a composition comprising at least one pigment and/or at least one filler that have been surface-treated beforehand as defined above and a composition comprising at least one electrophilic monomer as defined above and optionally at least one polymerization inhibitor.

According to one embodiment, in the kit in accordance with the present disclosure, the composition comprising the at least one surface-treated pigment and/or at least one surface-treated filler also comprises at least one nucleophilic agent as defined above.

According to another embodiment, in the kit in accordance with the present disclosure, the kit also contains a composition comprising at least one nucleophilic agent as defined above.

According to yet another embodiment of the present disclosure, the composition comprising the at least one surface-treated pigment and/or at least one surface-treated filler and the composition comprising the at least one electrophilic monomer and optionally the at least one polymerization inhibitor are present in the same anhydrous composition.

According to a further embodiment, the composition comprising the at least one surface-treated pigment and/or at least one surface-treated filler is an aqueous composition and the composition comprising the at least one electrophilic monomer and optionally the at least one polymerization inhibitor is an anhydrous composition.

The at least one electrophilic monomer is present in the composition comprising them in an amount generally ranging from 0.05% to 30% by weight, for example, from 0.01% to 50% by weight, or from 0.1% to 20% by weight relative to the total weight of the composition.

Further disclosed herein is a method for treating keratin fibers comprising applying to the keratin fibers a composition as defined above.

When the composition comprises at least one surface-treated pigment, the treatment of the keratin fibers is a dyeing treatment.

When the composition comprises at least one surface-treated filler, the treatment of the keratin fibers is a care treatment.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Example 1:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Cellulose-coated yellow iron oxide sold under the reference C2-5 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The lock obtained had a soft feel.

Example 2:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with $C_9$-$C_{15}$ perfluoroalkyl phosphate sold under the reference PF5 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The dye composition showed good stability over time.

Example 3:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with polymethylhydrogenosiloxane sold under the reference SI01-2 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The dye composition showed good stability over time.

Example 4:

The composition below was prepared:

| Ingredient | Amount |
| --- | --- |
| A-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with acrylate/dimethicone copolymer sold under the reference ASC-7 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The cosmetic properties of the lock obtained were very satisfactory.

Example 5:

The composition below was prepared:

| Ingredient | Amount |
| --- | --- |
| A-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with isopropyl containing a triisostearate sold under the reference ITT-2 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The cosmetic properties of the lock were very satisfactory.

Example 6:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with lauroyllysine sold under the reference LLD-5 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The lock obtained had a soft feel.

Example 7:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with polymethylhydrogenosiloxane and perfluoroalkyl phosphate sold under the reference FS01-52 Yellow LL-100 PD by the company Daito Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The dye composition showed good stability over time.

Example 8:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with isostearyl sebacate sold under the reference HS-C33-8073-10 by the company Miyoshi Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The cosmetic properties of the lock obtained were very satisfactory.

Example 9:

The composition below was prepared:

| Ingredient | Amount |
| --- | --- |
| α-ω Dihydroxylated polydimethylsiloxane/ cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with aluminium dimyristate sold under the reference MI-C33-8073-10 by the company Miyoshi Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The cosmetic properties of the lock obtained were very satisfactory.

Example 10:

The composition below was prepared:

| Ingredient | Amount |
| --- | --- |
| α-ω Dihydroxylated polydimethylsiloxane/ cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with disodium stearoyl glutamate sold under the reference NAI-C33-8073-10 by the company Miyoshi Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The lock obtained had a natural feel.

Example 11:

The composition below was prepared:

| Ingredient | Amount |
| --- | --- |
| α-ω Dihydroxylated polydimethylsiloxane/ cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Yellow iron oxide coated with PEG-12 dimethicone sold under the reference Yellow Iron Oxide AQ R0402 by the company LCW | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed yellow and the coloration obtained was shampoo-fast. The lock obtained had a natural feel.

Example 12:

The composition below was prepared:

| Ingredient | Amount |
| --- | --- |
| α-ω Dihydroxylated polydimethylsiloxane/ cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| D&C Red 7 coated with methylhydrogenopolysiloxane sold under the reference SI-D&C Red 7 by the company Miyoshi Kasei | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed red and the remanence of the coloration obtained was good, especially with respect to shampooing.

Example 13:

The composition below was prepared:

| Ingredient | Amount |
| --- | --- |
| α-ω Dihydroxylated polydimethylsiloxane/ cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 40 g |
| Nacre mica-titanium oxide-iron oxide coated with isopropyl titanium triisostearate sold under the reference KTZ Aruban Coral 12 by the company Taizhu | 10 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed orange and the coloration obtained was shampoo-fast. The lock obtained had a natural feel.

Example 14:

The composition below was prepared:

| Ingredient | Amount |
| --- | --- |
| α-ω Dihydroxylated polydimethylsiloxane/ cyclopentadimethylsiloxane (14.7/85.3) sold by Dow Corning under the name DC 1501 Fluid | 40 g |
| Cyclopentadimethylsiloxane sold by Dow Corning under the name DC 245 Fluid | 37 g |
| Mica-brown iron oxide sold under the reference Prestige Bronze by the company Eckart | 10 g |

-continued

| Ingredient | Amount |
| --- | --- |
| Talc coated with polydimethylsiloxane sold under the reference J-68-SAT by the company US Cosmetics | 3 g |
| Methylheptyl cyanoacrylate from Chemence | 10 g |
| Acetic acid | 0.25 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock was dyed bronze and the coloration obtained was shampoo-fast. The lock obtained had a soft feel.

Example 15:

The composition below was prepared:

| Ingredient | Amount |
| --- | --- |
| α-ω Dihydroxylated polydimethylsiloxane/cyclopentadimethylsiloxane (14.7/85.3) sold by Dow Corning under the name DC 1501 Fluid | 45 g |
| Cyclopentadimethylsiloxane sold by Dow Corning under the name DC 245 Fluid | 42 g |
| Talc coated with polydimethylsiloxane sold under the reference J-68-SAT by the company US Cosmetics | 3 g |
| Methylheptyl cyanoacrylate from Chemence | 10 g |

0.5 g of this composition was applied to a 1 g lock of clean, wet natural grey hair comprising 90% white hairs. After a leave-on time of 15 minutes at room temperature, the lock was dried with a hairdryer for two minutes.

The lock had a soft feel and was shampoo-fast.

What is claimed is:

1. A composition for treating keratin materials, comprising, in a cosmetically acceptable medium,
    at least one electrophilic monomer and
    at least one pigment and at least one filler that have been surface-treated beforehand with at least one organic agent,
    wherein
    the at least one surface-treated filler is present in the composition in an amount ranging from 0.05% to 95% by weight relative to the total weight of the composition; and
    the at least one surface-treated pigment and the at least one surface-treated filler are not chosen from micas coated with titanium and with at least one organic pigment.

2. The composition according to claim 1, wherein the at least one pigment is organic and chosen from nitroso, nitro, azo, xanthene, quinoline, anthraquinone, phthalo-cyanin, metal complex, isoindolinone, isoindoline, quinacridone, perinone, perylene, diketopyrrolopyrrole, thioindigo, dioxazine, triphenylmethane, and quinophthalone pigments.

3. The composition according to claim 1, wherein the at least one pigment is chosen from composite pigments comprising particles comprising an inorganic nucleus at least partially coated with an organic pigment and at least one binder for fixing the organic pigments to the nucleus.

4. The composition according to claim 1, wherein the at least one pigment is chosen from lakes comprising an inorganic substrate chosen from alumina, silica, calcium sodium borosilicate, calcium aluminium borosilicate, and aluminium onto which is adsorbed at least one organic dye.

5. The composition according to claim 1, wherein the at least one pigment is a pigment with special effects chosen from nacreous pigments, pigments with interference effects that are not fixed to a substrate, fluorescent pigments, phosphorescent pigments, photochromic pigments, thermochromic pigments, and quantum dots.

6. The composition according to claim 1, wherein the at least one pigment is a nacreous pigment chosen from mica coated with titanium and with at least one oxide chosen from iron oxides and chromium oxide, and nacreous pigments based on bismuth oxychloride.

7. The composition according to claim 1, wherein the at least one pigment is a mineral chosen from zirconium oxides, cerium oxides, iron oxides, chromium oxides, manganese violet, ultramarine blue, chromium hydrate, ferric blue, and titanium dioxide.

8. The composition according to claim 1, wherein the at least one filler is chosen from talc, natural or synthetic mica, silica, kaolin, bismuth oxychlorides, precipitated calcium carbonate, magnesium carbonate, magnesium hydrogen carbonate, hydroxyapatite, hollow silica microspheres, and glass or ceramic microcapsules.

9. The composition according to claim 1, wherein the at least one filler is chosen from:
    polyamide, poly-β-alanine, and polyethylene powders, tetrafluoroethylene polymer powders, lauroyllysine, starch, boron nitride, and acrylic acid polymer powders;
    silicone resin microbeads;
    acrylic polymer microspheres;
    polyurethane powders;
    metal soaps derived from organic carboxylic acids comprising from 8 to 22 carbon atoms;
    microcapsules of methyl acrylate or methacrylate polymers or copolymers, and microcapsules of vinylidene chloride and acrylonitrile copolymers; and
    elastomeric crosslinked organopolysiloxane powders.

10. The composition according to claim 1, wherein the at least one filler has an apparent diameter ranging from 0.01 to 150 μm.

11. The composition according to claim 1, wherein the at least one organic agent is chosen from amino acids; waxes; fatty acids and fatty alcohols, and derivatives thereof; anionic surfactants; lecithins; sodium, potassium, magnesium, iron, titanium, zinc or aluminium salts of fatty acids; metal alkoxides; polysaccharides; polyethylene; (meth)acrylic polymers; polymers and copolymers containing acrylate units; proteins; alkanolamines; silicone compounds; organofluorine compounds; and fluorosilicone compounds.

12. The composition according to claim 11, wherein the at least one organic agent is chosen from PEG-silicones; chitosan; triethoxycaprylylsilane; methicones; dimethicones; dimethicone/trimethyl siloxysilicates; lauroyllysine; lauroyllysine dimethicones; magnesium myristate; aluminium dimyristate; perfluoropolymethyl isopropyl ether; isostearyl sebacate; disodium stearoyl glutamate; dimethicone/disodium stearoyl glutamate; perfluoroalkyl phosphates; acrylate/dimethicone copolymer and perfluoroalkyl phosphate combinations; polymethylhydrogenosiloxane/perfluoroalkyl phosphates; lauroyllysine/aluminium tristearate; octyltriethylsilane; octyltriethylsilane and perfluoroalkyl phosphate combinations; acrylate/dimethicone copolymers; isopropyl titanium triisostearate; microcrystalline cellulose and carboxymethylcellulose; cellulose; acrylate copolymers; and perfluoroalkyl phosphate/isopropyl titanium triisostearate.

13. The composition according to claim 1, wherein which the at least one surface-treated pigment and at least one surface-treated filler are coated with at least one organic layer.

14. The composition according to claim 1, wherein the at least one organic agent is deposited onto the at least one pigment and the at least one filler by a method chosen from evaporation of solvent, chemical reaction between the molecules of the surface agent, and creation of a covalent bond between the surface agent and the at least one pigment and at least one filler.

15. The composition according to claim 14, wherein the at least one organic agent is covalently bonded to the at least one pigment and the at least one filler.

16. The composition according to claim 1, wherein the at least one organic agent is present in the composition in an amount ranging from 0.1% to 50% by weight relative to the total weight of the at least one surface-treated pigment and at least one surface-treated filler.

17. The composition according to claim 1, wherein the at least one surface-treated pigment is present in the composition in an amount ranging from 0.05% to 50% by weight relative to the total weight of the composition.

18. The composition according to claim 1, further comprising at least one surface-untreated filler.

19. The composition according to claim 1, further comprising at least one surface-untreated pigment.

20. The composition according to claim 1, wherein the at least one electrophilic monomer is chosen from compounds of formula (I):

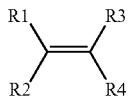

wherein:
$R_1$ and $R_2$, which may be identical or different, are chosen from sparingly electron-withdrawing groups and non-electron-withdrawing groups; and
$R_3$ and $R_4$, which may be identical or different, are chosen from electron-withdrawing groups.

21. The composition according to claim 20, wherein $R_1$ and $R_2$, which may be identical or different, are chosen from hydrogen; linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR, —COOR, —COR, —SH, —SR, —OH, and halogen atoms; modified or unmodified polyorganosiloxane residues; polyoxyalkylene groups; wherein R is chosen from linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR', —COOR', —COR', —SH, —SR', and —OH groups, halogen atoms, and polymer residues, wherein R' is chosen from $C_1$-$C_{10}$ alkyl radicals.

22. The composition according to claim 20, wherein $R_3$ and $R_4$, which may be identical or different, are chosen from —N(R)$_3^+$, —S(R)$_2^+$, —SH$_2^+$, —NH$_3^+$, —NO$_2$, —SO$_2$R, —C≡N, —COOH, —COOR, —COSR, —CONH$_2$, —CONHR, —F, —Cl, —Br, —I, —OR, —COR, —SH, —SR, and —OH groups, linear or branched alkenyl groups, linear or branched alkynyl groups, $C_1$-$C_4$ monofluoroalkyl or polyfluoroalkyl groups, aryl and aryloxy groups; wherein R is chosen from linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR', —COOR', —COR', —SH, —SR', and —OH groups, halogen atoms, and polymer residues, wherein R' is chosen from $C_1$-$C_{10}$ alkyl radicals.

23. The composition according to claim 1, wherein the at least one electrophilic monomer is chosen from monomers of the cyanoacrylate family of formula (II):

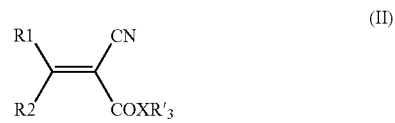

wherein:
X is chosen from NH, S, and 0;
R'$_3$ is chosen from hydrogen and R groups;
(II)
$R_1$ and $R_2$, which may be identical or different, are chosen from hydrogen; linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR, —COOR, —COR, —SH, —SR, —OH, and halogen atoms; modified or unmodified polyorganosiloxane residues; polyoxyalkylene groups; wherein R is chosen from linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR', —COOR', —COR', —SH, —SR', and —OH groups, halogen atoms, and polymer residues, wherein A' is chosen from $C_1$-$C_{10}$ alkyl radicals.

24. The composition according to claims 20, wherein $R_1$ and $R_2$ are hydrogen.

25. The composition according to claim 23, wherein X is O.

26. The composition according to claim 23, wherein R'$_3$ is chosen from $C_6$-$C_{10}$ alkyl radicals.

27. The composition according to claim 1, wherein the at least one electrophilic monomer is chosen from monomers of the alkyl or alkoxyalkyl 2-cyanoacrylate family of formula (VI):

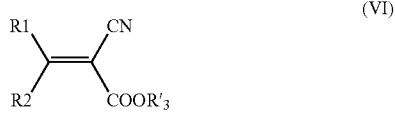

wherein:
R'$_3$ is chosen from $C_1$-$C_{10}$ alkyl radicals, $C_2$-$C_{10}$ alkenyl radicals, and ($C_1$-$C_4$)alkoxy($C_1$-$C_{10}$)alkyl radicals;
$R_1$ and $R_2$, which may be identical or different, are chosen from hydrogen; linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR, —COOR, —COR, —SH, —SR, —OH, and halogen atoms; modified or unmodified polyorganosiloxane residues; polyoxyalkylene groups; wherein R is chosen from linear, branched, or cyclic, saturated or unsaturated hydrocarbon-based groups comprising from 1 to 20 carbon atoms and optionally comprising at least one atom chosen from nitrogen, oxygen, and sulfur atoms, and optionally substituted with at least one group chosen from —OR', —COOR', —COR', —SH, —SR', and —OH groups, halogen atoms, and polymer residues, wherein R' is chosen from $C_1$-$C_{10}$ alkyl radicals.

28. The composition according to claim 27, wherein $R'_3$ is chosen from $C_6$-$C_{10}$ alkyl radicals.

29. The composition according to claim 27, wherein $R_1$ and $R_2$ are hydrogen.

30. The composition according to claim 1, wherein the at least one electrophilic monomer is chosen from compounds of formula (VII) and mixtures thereof:

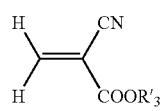

(VII)

wherein $R'_3$ is chosen from the following radicals:
- —(CH$_2$)$_7$—CH$_3$;
- —CH(CH$_3$)—(CH$_2$)$_5$—CH$_3$;
- —CH$_2$—CH(C$_2$H$_5$)—(CH$_2$)$_3$—CH$_3$;
- —(CH$_2$)$_5$—CH(CH$_3$)—CH$_3$; and
- —(CH$_2$)$_4$—CH(C$_2$H$_5$)—CH$_3$.

31. The composition according to claim 1, wherein the at least one electrophilic monomer is present in the composition in an amount ranging from 0.1% to 80% by weight relative to the total weight of the composition.

32. The composition according to claim 1, wherein the cosmetically acceptable medium is anhydrous.

33. The composition according to claim 32, wherein the cosmetically acceptable medium is chosen from:
- aromatic alcohols;
- fatty alcohols;
- modified or unmodified polyols;
- volatile or non-volatile silicones;
- mineral, organic or plant oils;
- oxyethylenated or non-oxyethylenated waxes, paraffins and alkanes;
- fatty acids, fatty amides and fatty esters; and mixtures thereof.

34. The composition according to claim 1, further comprising at least one nucleophilic agent.

35. The composition according to claim 34, wherein the at least one nucleophilic agent is water.

36. A process for treating keratin fibers, comprising applying a composition to the keratin fibers in the presence of at least one nucleophilic agent,
wherein the composition comprises, in a cosmetically acceptable medium,
at least one electrophilic monomer and
at least one pigment and at least one filler that have been surface-treated beforehand with at least one organic agent,
wherein
the at least one surface-treated filler is present in the composition in an amount ranging from 0.05% to 95% by weight relative to the total weight of the composition; and
the at least one surface-treated pigment and the at least one surface-treated filler are not chosen from micas coated with titanium and with at least one organic pigment.

37. The process according to claim 36, comprising applying said composition to the keratin fibers in at least two steps, wherein one of the steps comprises applying to the keratin fibers a composition comprising the at least one surface-treated pigment and/or the at least one surface-treated filler, and the other step comprises applying to the keratin fibers a composition comprising the at least one electrophilic monomer, the order of the steps being irrelevant.

38. The process according to claim 36, wherein the at least one nucleophilic agent is applied separately.

39. The process according to claim 36, wherein the at least one nucleophilic agent is present in the composition comprising the at least one surface-treated pigment.

40. The process according to claim 36, comprising a step comprising applying to the keratin fibers at least one keratin-reducing agent, before applying the composition to the keratin fibers.

41. A kit for treating keratin fibers, comprising a composition comprising at least one electrophilic monomer and optionally at least one polymerization inhibitor and a composition comprising, in a cosmetically acceptable medium, at least one electrophilic monomer and at least one pigment and at least one filler that have been surface-treated beforehand with at least one organic agent, wherein the at least one surface-treated filler is present in the composition in an amount ranging from 0.05% to 95% by weight relative to the total weight of the composition; and the at least one surface-treated pigment and the at least one surface-treated filler are not chosen from micas coated with titanium and with at least one organic pigment.

42. The kit according to claim 41, wherein the composition comprising the at least one surface-treated pigment and at least one surface-treated filler also comprises at least one nucleophilic agent.

43. The kit according to claim 41, further comprising a composition comprising at least one nucleophilic agent.

44. The kit according to claim 41, wherein the composition comprising the at least one surface-treated pigment and the at least one surface-treated filler and the composition comprising the at least one electrophilic monomer and optionally the at least one polymerization inhibitor are present in the same anhydrous composition.

45. The kit according to claim 41, wherein the composition comprising the at least one surface-treated pigment and the at least one surface-treated filler is an aqueous composition and the composition comprising the at least one electrophilic monomer and optionally the at least one polymerization inhibitor is an anhydrous composition.

46. The composition according to claim 19, wherein the surface-untreated pigment is chosen from mica coated with titanium and with at least one organic pigment.

* * * * *

UNITED STATES PATENT AND TRADEMARK OFFICE
CERTIFICATE OF CORRECTION

PATENT NO. : 7,621,966 B2
APPLICATION NO. : 11/544576
DATED : November 24, 2009
INVENTOR(S) : Gaëlle Brun It is certified that error appears in the above-identified patent and that said Letters Patent is hereby corrected as shown below:

In Claim 37, column 30, line 16, "and/or" should read --and--.

Signed and Sealed this

Sixteenth Day of March, 2010

David J. Kappos
*Director of the United States Patent and Trademark Office*